(12) United States Patent  (10) Patent No.: US 8,878,147 B2
Robinson  (45) Date of Patent: Nov. 4, 2014

(54) METHOD AND APPARATUS FOR IN SITU PREPARATION OF SERIAL PLANAR SURFACES FOR MICROSCOPY

(71) Applicant: Joseph C. Robinson, Portland, OR (US)

(72) Inventor: Joseph C. Robinson, Portland, OR (US)

(*) Notice: Subject to any disclaimer, the term of this patent is extended or adjusted under 35 U.S.C. 154(b) by 0 days.

(21) Appl. No.: 13/745,584

(22) Filed: Jan. 18, 2013

(65) Prior Publication Data
US 2013/0174301 A1 Jul. 4, 2013

Related U.S. Application Data

(63) Continuation-in-part of application No. 13/227,441, filed on Sep. 7, 2011.

(60) Provisional application No. 61/380,631, filed on Sep. 7, 2010.

(51) Int. Cl.
| | |
|---|---|
| *G21K 5/10* | (2006.01) |
| *B23K 15/00* | (2006.01) |
| *H01J 37/26* | (2006.01) |
| *G01Q 60/24* | (2010.01) |
| *G01Q 30/20* | (2010.01) |
| *G02B 21/26* | (2006.01) |
| *H01J 37/20* | (2006.01) |
| *B82Y 35/00* | (2011.01) |
| *G01N 1/28* | (2006.01) |

(52) U.S. Cl.
CPC ......... *B23K 15/0006* (2013.01); *H01J 37/261* (2013.01); *G01Q 60/24* (2013.01); *G01Q 30/20* (2013.01); *G02B 21/26* (2013.01); *H01J 37/20* (2013.01); *B82Y 35/00* (2013.01); *H01J 2237/2809* (2013.01); *H01J 2237/31745* (2013.01); *G01N 2001/2886* (2013.01)

USPC ............... 250/492.1; 250/492.21; 250/492.2; 250/492.3

(58) Field of Classification Search
None
See application file for complete search history.

(56) References Cited

U.S. PATENT DOCUMENTS

| 3,614,423 A | * | 10/1971 | Heynick et al. ............... 204/193 |
| 3,622,782 A | | 11/1971 | Smith et al. |
| 4,128,765 A | | 12/1978 | Franks |

(Continued)

FOREIGN PATENT DOCUMENTS

JP  09306403 A  * 11/1997

OTHER PUBLICATIONS

V. V. Pletnev et al., "Coefficient of Surface Sputtering of Solids by Light Ions", translated from Atomnaya Energiya, vol. 69, No. 2, Aug. 1990 (original article submitted Sep. 26, 1988), pp. 104-106.

(Continued)

*Primary Examiner* — Andrew Smyth
(74) *Attorney, Agent, or Firm* — Kolisch Hartwell, P.C.

(57) ABSTRACT

Systems and methods for preparing solid samples for analysis, such as microscopic examination in cross section or planimetric orientation. The sample preparation systems may include a sample support configured to secure a solid sample, an excitation beam source that generates an excitation beam configured to remove material from a surface of the sample, a beam shield configured to at least partially protect the sample from the excitation beam, and a beam shield holder configured to secure the beam shield, where the adjustment of the relative positions of the beam shield and sample holder permits the excitation beam to selectively expose a series of substantially planar surfaces of the sample.

23 Claims, 3 Drawing Sheets

(56) References Cited

U.S. PATENT DOCUMENTS

| | | | |
|---|---|---|---|
| 4,381,453 | A | 4/1983 | Cuomo et al. |
| 4,574,179 | A | 3/1986 | Masuzawa et al. |
| 4,658,143 | A | 4/1987 | Tokiguchi et al. |
| 4,887,282 | A * | 12/1989 | Mueller .................. 378/34 |
| 5,472,566 | A | 12/1995 | Swann et al. |
| 5,907,157 | A | 5/1999 | Yoshioka et al. |
| 5,986,264 | A | 11/1999 | Grunewald |
| 6,333,485 | B1 * | 12/2001 | Haight et al. ............ 219/121.68 |
| 6,710,918 | B2 | 3/2004 | Birk et al. |
| 6,768,110 | B2 | 7/2004 | Alani |
| 7,552,524 | B2 * | 6/2009 | Ma et al. .................. 29/603.16 |
| 7,700,931 | B2 | 4/2010 | Shichi et al. |
| 8,283,642 | B2 * | 10/2012 | Coyle et al. ............. 250/492.21 |
| 8,592,763 | B2 * | 11/2013 | Coyle et al. ................ 250/309 |
| 2002/0030800 | A1 * | 3/2002 | Nellissen ........................ 355/53 |
| 2002/0084422 | A1 * | 7/2002 | Kienzle et al. ......... 250/396 ML |
| 2005/0081997 | A1 * | 4/2005 | Yoshioka et al. .......... 156/345.3 |
| 2005/0266680 | A1 * | 12/2005 | Daskal et al. ................ 438/637 |
| 2006/0134885 | A1 * | 6/2006 | Yamazaki et al. ............ 438/460 |
| 2007/0028444 | A1 * | 2/2007 | Kasuga et al. .................. 29/742 |
| 2008/0067443 | A1 * | 3/2008 | Todoroki et al. ......... 250/492.21 |
| 2008/0135779 | A1 * | 6/2008 | Shichi et al. ............. 250/440.11 |
| 2009/0095923 | A1 * | 4/2009 | Gierak ..................... 250/492.21 |
| 2010/0099224 | A1 * | 4/2010 | Aoki et al. .................... 438/127 |
| 2010/0181288 | A1 * | 7/2010 | Tang et al. ...................... 216/45 |
| 2012/0085923 | A1 * | 4/2012 | Coyle et al. ............. 250/453.11 |
| 2012/0085937 | A1 * | 4/2012 | Coyle et al. ................ 250/492.3 |
| 2012/0085938 | A1 * | 4/2012 | Coyle et al. ................ 250/492.3 |

OTHER PUBLICATIONS

Richard Haight et al., "MARS: Femtosecond laser mask advanced repair system in manufacturing", Journal of Vacuum Science and Technology B: Microelectronics and Nanometer Structures, vol. 17, Issue 6, 1999, pp. 3137-3143.

R. Alani et al., "Instrumentation for SEM Specimen Preparation of Semiconductors", Recent Advances in Broad Ion Beam Techniques, Semiconductor International, Feb. 1, 2000, 5 pgs.

R.M. Langford et al., "Broad ion beam milling of focused ion beam prepared transmission electron microscopy cross sections for high resolution electron microscopy", Journal of Vacuum Science and Technology A: Vacuum, Surfaces, and Films, vol. 19, Issue 3, May 2001, pp. 982-985.

W. Hauffe et al., "3D Microscopy and Microanalysis of Heterogeneous SEM Samples by Broad Ion Beam Processing: Cutting—Etching—Coating", Microscopy and Microanalysis, vol. 8, Supplement S02, 2002, pp. 552-553.

Alfred Wagner et al., "MARS2: An Advanced Femtosecond Laser Mask Repair Tool", IBM Semiconductor Research and Development Center (SRDC) Research Division, Yorktown Heights, NY, Dec. 27, 2002, 12 pgs.

W. Hauffe, "Broad Ion Beam (BIB) Slope Cutting Through Sn-Coated Copper Wires for 3D Scanning Electron Microscopy and Microanalysis", Microscopy and Microanalysis, vol. 13, Supplement S02, 2007, pp. 1526-1527.

Kazumichi Ogura et al., "New Methods for Cross-Section Sample Preparation Using Broad Argon Ion Beam", Microscopy and Microanalysis, vol. 13, Supplement S02, 2007, pp. 1518-1519.

N.S. Smith et al., "A high brightness source for nano-probe secondary ion mass spectrometry", Applied Surface Science, vol. 255, Issue 4, Dec. 15, 2008, available for download May 14, 2008, pp. 1606-1609.

Kenneth MaClean et al., "Measuring Charge Transport in a Thin Solid Film Using Charge Sensing", ACS Publications, NANO Letters, vol. 10(3), Feb. 23, 2010, pp. 1037-1040.

M. Petzold et al., "Micro Structure Analysis for System in Package Components—Novel Tools for Fault Isolation, Target Preparation, and High-Resolution Material Diagnostics", 60th Electronic Components and Technology Conference, Part 2 : Jun. 1-4, 2010, pp. 1296-1302.

* cited by examiner

METHOD AND APPARATUS FOR IN SITU PREPARATION OF SERIAL PLANAR SURFACES FOR MICROSCOPY

CROSS-REFERENCE TO RELATED APPLICATIONS

This application is a continuation-in-part of U.S. patent application Ser. No. 13/227,441, filed Sep. 7, 2011 and entitled "METHOD AND APPARATUS FOR PREPARING SERIAL PLANAR CROSS SECTIONS", which application claims the benefit under 35 U.S.C. §119(e) of U.S. Provisional Patent Application Ser. No. 61/380,631 titled SYSTEM FOR IN SITU PREPARATION OF PLANAR SURFACES filed Sep. 7, 2010, which are hereby incorporated by reference.

TECHNICAL FIELD

This application is directed to the preparation of samples for microscopy. In particular, the application is directed to the preparation of sequential planar surfaces on a microscopy sample.

BACKGROUND

The ongoing revolution in the preparation of nano-engineered materials continues to spawn new combinations of elements and compounds. Many of these new materials may include exotic phase mixtures (composites) or layered thin film structures (devices), resulting in new and unusual properties that may result directly from the spatial relationships and nano-structural arrangements of the material components. Increasingly, these new materials must be characterized at the molecular or atomic level using microscopy techniques such as Scanning Probe Microscopy (SPM), Transmission Electron Microscopy (TEM), and Scanning Electron Microscopy (SEM), among others.

Sample preparation for multi-phase materials traditionally involves embedding the sample in a support matrix followed by abrasive polishing or microtome slicing to achieve a smooth surface or thin section. In the case of layered thin film devices, the samples were generally cleaved (broken) or otherwise cut into smaller pieces, sandwiched between support materials, and then polished smooth. These techniques were well-suited for materials that could withstand abrasive reduction and where charging effects could be circumvented by the addition of a conductive path.

The use of focused ion beam (FIB) systems has became a valuable, albeit time consuming, tool for sampling precise site-specific sub-surface features in multi-phase materials or thin film devices. Though FIBs have become faster at removing a wide range of materials, the excavated area is typically very small (2,000 $\mu m^3$). In addition, many novel materials may contain organic fibers and polymers, rendering them less suitable for FIB milling due to an associated charge build-up or adverse sputtering properties.

Increasingly, new combinations of exotic materials used in multi-phase and multi-layered thin films are poorly-suited to either mechanical polishing or FIB milling. Softer materials tend to smear or become delaminated from neighboring structures, while hard or brittle materials may fracture or shed particles into neighboring regions, either result constituting an unacceptable alteration of the original structure of the sample material. Similarly, composite materials may exhibit distortion of discrete grains or phases as a result of the shearing forces of polishing, altering critical spatial information and introducing chemical anomalies that affect subsequent EDX or surface analysis results.

Examples of sample preparation and microscopic analyses may be found in the following references: Alani et al., Instrumentation for SEM Specimen Preparation of Semiconductors, Recent Advances in Broad Ion Beam Techniques, Feb. 1, 2000; Smith et al., Applied Surface Science 255 (2008) 1606-1609; Langford et al., J. Vac. Sci. Technol. A19, 982 (2001); Hauffe et al., 3D Microscopy and Microanalysis of Heterogeneous SEM Samples by Broad Ion Beam Processing: Cutting-Etching-Coating, 1997; Hauffe, Broad Ion Beam (BIB) Slope Cutting through Sn-Coated Copper Wires for 3D Scann9ing Electron Microscopy and Microanalysis, Microsc Microanal 13 (Suppl 2) 2007; Ogura et al., New Methods for Cross-Section Sample Preparation Using Broad Argon Ion Beam, Microsc Microanal 13 (Suppl 2), 2007; Haight et al., J. Vac. Sci. Technol. B 17, 3137 (1999); MacLean et al., Nano Lett., 2010, 10(3), pp 1037-1040; Petzold et al., Micro Structure Analysis for System in Package Components—Novel Tools for Fault Isolation, Target Preparation, and High-resolution Material Diagnostics, Electronic Components and Technology Conference ECTC, Las Vegas, Session 29, Apr. 6, 2010, each of which is hereby incorporated by reference.

Selected examples of sample preparation and microscopic analyses may be found in the following patent documents: Todoroki et al., U.S. Patent Appl. Publ., U.S. 2008/0067443 A1; Coyle et al., U.S. Patent Appl. Publ. 2012/0085923; Coyle et al., U.S. Patent Appl. Publ., 2012/0085937; Coyle et al., U.S. Patent Appl. Publ., 2012/0085938; Coyle et al., U.S. Patent Appl. Publ., 2012/0085939; Smith, U.S. Pat. No. 3,622,782; Franks, U.S. Pat. No. 4,128,765; Masuzawa et al., U.S. Patent No. 4,574,179; Tokiguchi et al., U.S. Pat. No. 4,658,143; Swann et al., U.S. Pat. No. 5,472,566; Yoshioka et al., U.S. Pat. No. 5,907,157; Grünewald, U.S. Pat. No. 5,986,264; Birk et al., U.S. Pat. No. 6,710,918; Alani, U.S. Pat. No. 6,768,110; Shichi et al., U.S. Pat. No. 7,700,931; Cuomo et al., U.S. Pat. No. 4,381,453; Haight et al., U.S. Pat. No. 6,333,485; Hasegawa, et al., U.S. Pat. No. 7,722,818; Sugizaki, U.S. Pat. No. 7,952,082; Kagaya, U.S. Pat. No. 8,008,635; Coyle, et al., U.S. Pat. No. 8,283,642, the disclosures of each of which are hereby incorporated by reference for any and all purposes.

SUMMARY

The invention includes systems and methods for preparing solid samples for analysis, such as microscopic analysis. In one embodiment of the invention, the sample preparation systems include a sample support configured to secure a solid sample, an excitation beam source that generates an excitation beam configured to remove material from a surface of the sample, a beam shield configured to at least partially protect the sample from the excitation beam, and a beam shield holder configured to secure the beam shield, where the adjustment of the relative positions of the beam shield and sample holder permits the excitation beam to selectively expose a series of substantially planar surfaces of the sample.

DETAILED DESCRIPTION

In 1991 Hauffe described and published a technique for masked broad ion beam milling of samples for microscopy whereby a thin layer of material is sputtered away from the top surface of a solid sample leaving a topographically planar surface acceptable for scanning electron microscopic examination and/or other analytical characterization methods. His method, commonly known as "slope cutting" uses a conventional broad ion beam directed at the sample parallel with its top surface. A beam shield is positioned just below the top surface of the sample exposing only the material protruding above the top edge of the beam shield. The top surface of the beam shield is beveled at an angle between 0° and 10° with respect to the sample surface and deflects part of the beam. When the beam strikes the beam shield and sample, the portion of the sample that protrudes above the beam shield is selectively sputtered. Over time, a uniform thickness of material is removed from a large area.

Sample preparation using Hauffe's technique is relatively time-consuming and unreliable. Capturing features in the desired cartesian plane and at the ideal depth is difficult using currently available commercial products. Some vendors provide rudimentary optical microscopes for ex situ alignment or process monitoring, but the long distance from the lens to the sample across a vacuum barrier limits the optical acuity that can be obtained. Finished samples must be transferred to a scanning electron microscope for verification and analysis. If the initial processing cycle does not capture the feature or features of interest in the desired plane, the sample must be removed from scanning electron microscope, remounted, realigned with respect to the beam shield, and re-processed. A single processing cycle can take from one to two hours. In addition, for those devices that employ a beam shield affixed to the sample itself (for example using an adhesive), reprocessing becomes virtually impossible.

The sample preparation method and apparatus disclosed herein occurs in situ, that is, inside the vacuum chamber of a scanning electron microscope or other vacuum instrument where the ongoing progress and quality of the surface can be monitored immediately following a reprocessing cycle via microscopic examination. Furthermore, by virtue of the in situ integration with a host vacuum instrument, additional analytical techniques data can potentially be employed contemporaneously, such as for example secondary electron, back-scattered electron, secondary ion Auger electron, EBSD, and energy or wavelength dispersive X-rays, among others. Furthermore, the processed sample is available for immediate viewing, thereby eliminating the formation of oxidative and other reactive artifacts.

Figure 1:
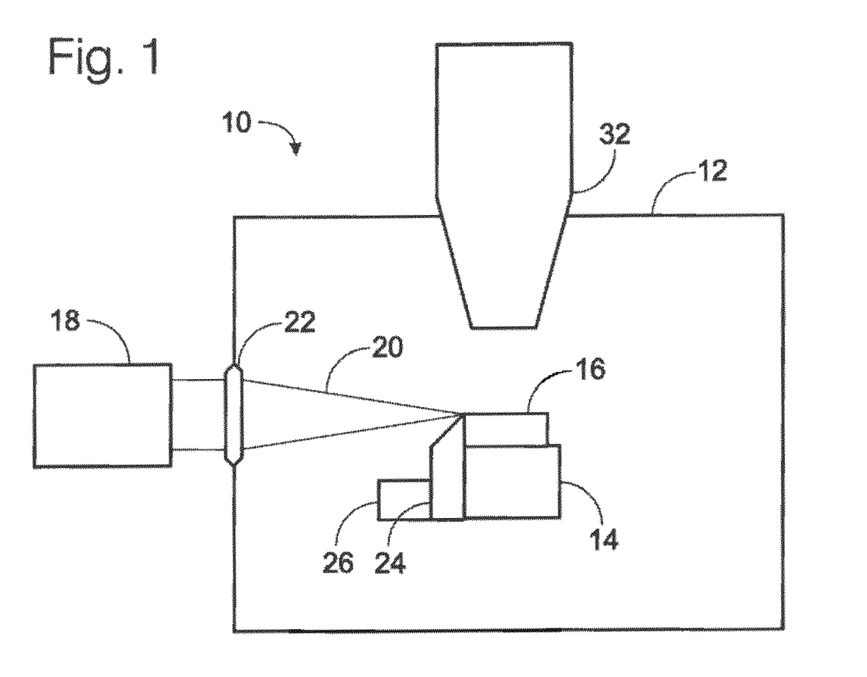
FIG. 1 is a schematic showing a sample preparation system according to an embodiment of the present invention.

FIG. 1 shows a schematic representation of a microscope or analytical instrument 10 incorporating a sample preparation system according to one embodiment of the present invention. The microscope or analytical instrument includes a vacuum chamber 12 for sample preparation and examination. Within the vacuum chamber 12 is a sample support 14 for securely mounting a solid sample 16 of interest. Sample support 14 may be or incorporate a microscope sub stage. Sample support 14 may include a positive-positioned self-aligning sample support configured to position sample 16 at a desired point in space for processing, for viewing the sample, or both.

In one embodiment, sample support 14 may incorporate a sample mounting surface, and a linear movement mechanism capable of moving the sample in two orthogonal directions relative to the sample viewing surface. Alternatively or in addition, the sample support 14 may incorporate a linear movement mechanism capable of movement in a direction perpendicular to the sample mounting surface. Alternatively or in addition, the sample support 14 may incorporate a rotation mechanism capable of rotation of the sample mounting surface (yaw).

The instrument 10 further includes an excitation beam source 18 configured to generate an excitation beam 20 that may be configured to remove material from the surface of the sample 16. The excitation beam of FIG. 1 may be focused by an appropriate focusing means, for example a focusing or diffractive lens 22.

A beam shield 24 may be position adjacent to the sample 16. The beam shield is configured to protect a portion of sample 14 from the excitation beam 20. Beam shield 24 is typically secured in a beam shield holder 26 that is itself configured to secure the beam shield. The beam shield holder 26 may be configured such that the position of the beam shield adjacent to the sample can be adjusted laterally, vertically, or both laterally and vertically. In addition and as discussed above, sample support 14 may permit rotation or yaw of the sample mounting surface, and in particular rotation or yaw of the sample mounting surface with respect to the beam shield.

In one embodiment, the sample support 14, or the beam shield holder 26, or both, are configured to be adjustable with respect to the position of the other. That is, the beam shield holder may be configured so that the relative position of the beam shield may be adjusted relative to the position of the sample. Alternatively or in addition, the sample support 14 may be configured so that the relative position of the sample may be adjusted relative to the position of the beam shield. The relative position adjustment may include lateral adjustment, vertical adjustment, or rotational adjustment (yaw) of one or both of the sample support and the beam shield with respect to the other.

The beam shield 24 and beam shield holder 26 are configured so that the beam shield can be vertically adjusted. For example, beam shield 24 may be sequentially lowered, and by progressively lowering the beam shield 24 adjacent the sample 16, the excitation beam 20 is permitted to selectively and sequentially mill a series of substantially planar surfaces from the solid sample.

The apparatus of FIG. 1 is designed and configured to prepare sequential planar surfaces on a single solid sample, facilitating simultaneous examination and analysis by a detector or detection system 32. The analytical instrument may be any instrument that would benefit from the ability to view the newly exposed sequential sections of a sample. Typically, the analytical instrument is a microscope, such as a light microscope (LM), scanning electron microscope (SEM), focused ion beam (FIB), or atomic force microscope (AFM), among others. The analytical instrument may incorporate any of a variety of detectors configured to collect characteristic signals, such as secondary electron, backscattered electron, secondary ion, Auger electron, X-ray photoelectrons, X-rays, or light. The surface preparation system disclosed herein does not interfere with any of the primary imaging or secondary analytical capabilities of the host vacuum instrument.

In one embodiment of the invention, the beam shield 24 is configured such that the vertical position of the beam shield adjacent to the sample 16 can be adjusted in small increments. As shown in FIGS. 2A-2D, such an adjustable beam shield can be used in conjunction with an excitation beam to progressively expose new sample surfaces.

Figure 2A:
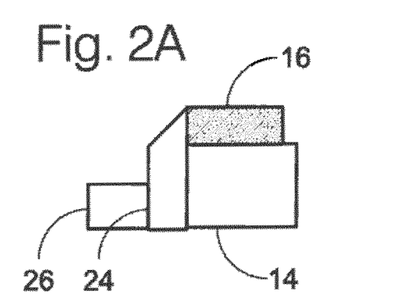
FIG. 2A depicts a schematic representation of a sample preparation system having an adjustable beam shield, according to an alternative embodiment of the invention.
Figure 2B:
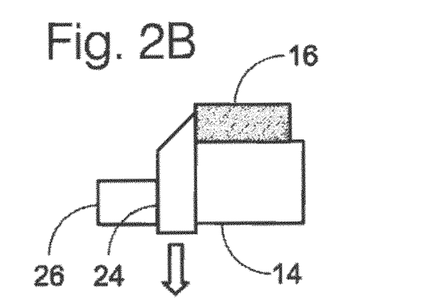
FIG. 2B depicts the beam shield being lowered by an incremental amount.
Figure 2C:
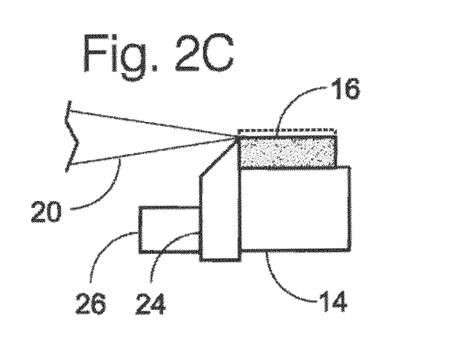
FIG. 2C depicts the removal of material from the sample surface using an excitation beam.
Figure 2D:
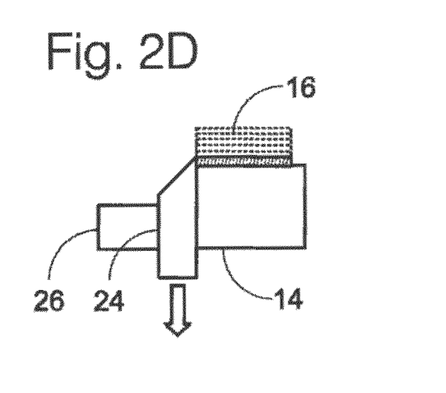
FIG. 2D depicts the sequential and incremental removal of material from the sample surface by progressively lowering the beam shield with respect to the sample.

FIG. 2A is a schematic representation of sample support 14, the sample of interest 16, beam shield 24, and beam shield holder 26 of the disclosed sample preparation system. FIG. 2B shows the beam shield after it has been lowered relative to the sample 16 by an incremental amount. As shown in FIG. 2C, excitation beam 20 may be used to remove the uppermost layer of sample 16, leaving the portion of the sample protected by the beam shield intact, where the dashed lane indicates the original dimensions of the sample 16. FIG. 2D represents a sequential and incremental removal of material from the sample surface by progressively lowering the beam shield with respect to the sample, as shown by the dashed lines which represent successive exposed surfaces of the sample.

In this embodiment, the beam shield of the device is typically placed and oriented such that the upper-most edge of the beam shield is positioned just below the sample surface and parallel to the normal surface of the sample. In one embodiment of the invention, the beam shield is positioned so that the edge of the beam shield is positioned about 10 µm or less below the surface of the sample. The upper part of the beam shield is typically beveled at an angle between 0 and 10 degrees from parallel to the sample surface plane and therefore at approximately 80 to 90 degrees from perpendicular to the side wall of the sample.

The surface preparation system is typically constructed so that the excitation source bombards both the beveled portion of the beam shield and the portion of the sample that is exposed above the beam shield. The excitation source may be any of a wide variety of energy beams that are suited for material removal. Selection of a particular beam species may depend on the nature of the sample, including sample integrity, desired material removal rates, susceptibility of the sample to heat damage, susceptibility of the sample to electrostatic charging, and the likelihood of artifact generation. Suitable excitation sources include (without limitation), electron beams, ion beams (such as LMIS, Plasma, Penning, etc.), X-rays, lasers and ultrafast lasers (including excimer lasers, $CO_2$ lasers, Nd/YAG lasers, and Ti-sapphire lasers, among others).

The excitation source typically produces a beam that is optimized for removing material from the sample such as by sputtering or ablation. During and after the surface processing (milling) cycles, the area processed by the excitation source may be simultaneously imaged by any conventional means, including optical or electron microscopy, among others.

Between surface processing (milling) cycles, the beam shield may be lowered an incremental vertical distance while the sample remains stationary. This facilitates the removal of additional material from the sample surface during the next surface processing (thinning) cycle. The subsequent material removed from the sample corresponds to the newly exposed area resulting from lowering the beam shield. Subsequent lowering of the beam shield removes incremental parallel slices of the sample from the same approximate lateral area. Where such sequentially exposed areas of the sample are imaged in sequence, the images may be used to reconstruct a 3-dimensional representation of various features previously embedded in the solid matrix of the sample. A variety of commercially available imaging software packages may be used to prepare such a reconstruction.

In order to achieve a substantially planar sample surface, the material removal process may require rotary oscillation of the sample through an arc around the beam axis center during the surface processing to prevent a "curtaining" affect caused by differential material removal rates in areas of the sample composed of materials having differing surface properties. In order to compensate for curtaining, the sample is rotated through an arc of variable angle optimized for minimal curtaining.

Figure 3A:
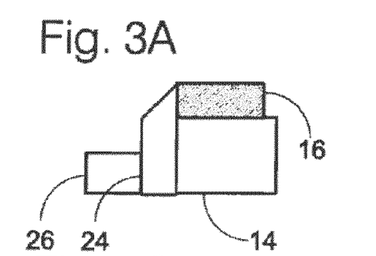
FIG. 3A depicts a schematic representation of a sample preparation system having an adjustable sample support according to yet another alternative embodiment of the invention.
Figure 3B:
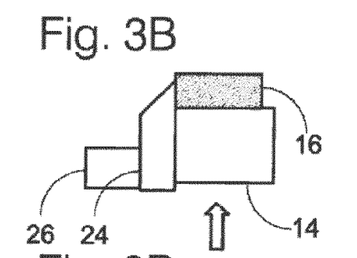
FIG. 3B depicts the sample being raised by an incremental amount.
Figure 3C:
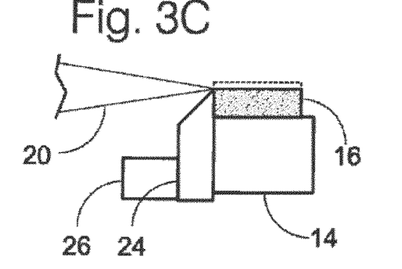
FIG. 3C depicts the removal of material from the sample surface using an excitation beam.
Figure 3D:
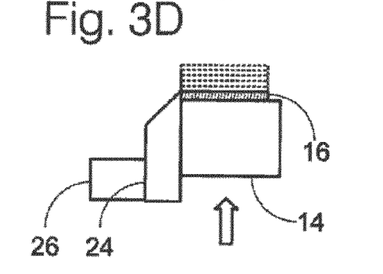
FIG. 3D depicts the sequential and incremental removal of material from the sample surface by progressively raising the sample with respect to the beam shield.

In an alternative embodiment, the sample holder 14 is configured such that the vertical position of the sample adjacent to the beam shield can be adjusted in small increments, as shown in FIGS. 3A-3D. FIG. 3A is a schematic representation of sample support 14, the sample of interest 16, beam shield 24, and beam shield holder 26 of the disclosed sample preparation system. FIG. 3B shows the sample position after the sample has been raised relative to the beam shield 24 by an incremental amount. As shown in FIG. 3C, excitation beam 20 may be used to remove the uppermost layer of sample 16, leaving the portion of the sample protected by the beam shield intact, where the dashed lane indicates the original dimensions of the sample 16. FIG. 3D represents a sequential and incremental removal of material from the sample surface by progressively raising the sample holder with respect to the beam shield, as shown by the dashed lines which represent successive exposed surfaces of the sample.

In this embodiment, between surface processing (milling) cycles, the sample may be raised an incremental vertical distance while the beam shield remains stationary, facilitating the removal of additional material from the sample surface during the next surface processing (thinning) cycle. The subsequent material removed from the sample corresponds to the newly exposed area resulting from raising the sample further, with respect to the beam shield. Subsequent raising of the sample removes incremental parallel slices of the sample from the same approximate lateral area. As discussed above, such sequentially exposed areas of the sample may be imaged in sequence and used to reconstruct a 3-dimensional model of the solid sample.

Figure 4:
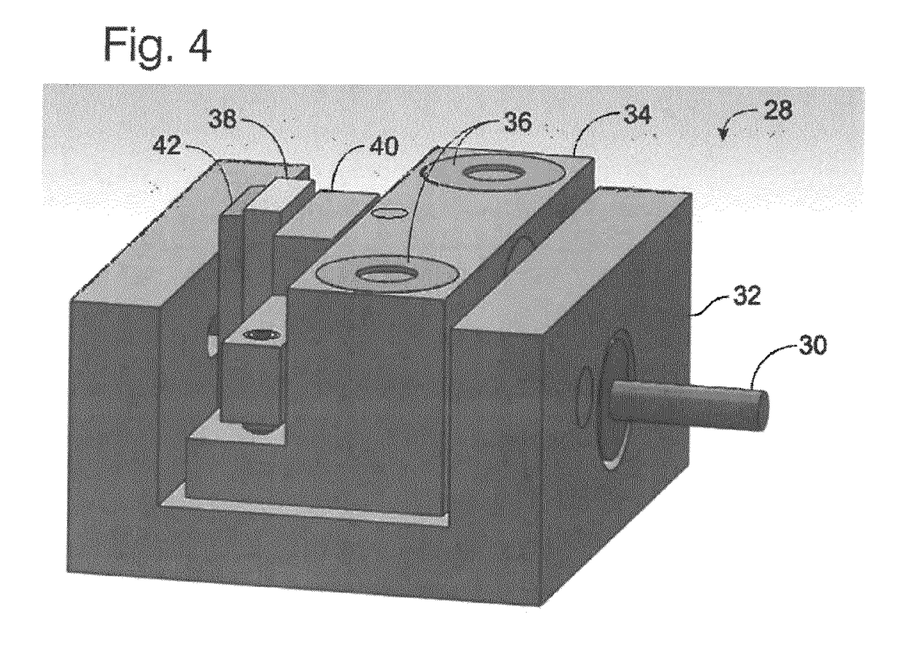
FIG. 4 is a perspective side view of a sample preparation system according to an alternative embodiment of the present invention.
Figure 5:
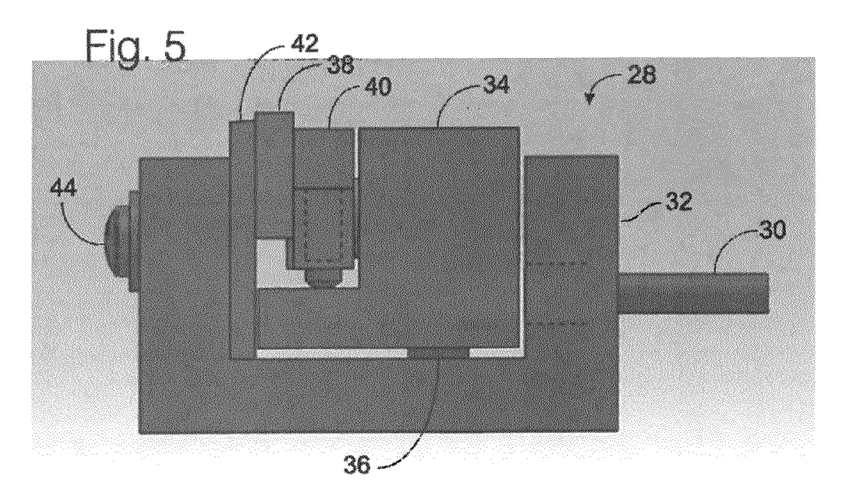
FIG. 5 is a side elevation of the sample preparation system of FIG. 4.

In yet another embodiment of the invention, the sample preparation system may include a sample support assembly 28, as shown in FIGS. 4 and 5. The sample support assembly 28 may include one or more mounting posts 30, for securing the support yoke 32 of the sample support assembly within a vacuum chamber associated with the desired analytical instrument. While the support yoke 32 remains fixed, the support yoke provides a foundation for a guide block 34, which is configured to translate along the Z-axis (or vertically, as depicted in FIGS. 4 and 5) along guide bushings 36.

As guide block 34 is translated along the Z-axis, the sample 38 is also translated along the Z-axis, by virtue of the sample being secured to the guide block 34 by the sample clamp pivot support 40. Beam shield 42, adjacent to sample 38, does not translate vertically with the guide block 34. As shown in FIG. 5 in particular, the beam shield 42 is not coupled to guide block 34, but is instead secured to the support yoke by a beam shield fastener 44. The sample support assembly 28 is therefore configured to selectively expose a series of substantially planar surfaces of the solid sample 38 by incrementally adjusting the vertical position of the sample with respect to the beam shield 42, as depicted in FIG. 3A-3D.

The surface preparation system of the disclosure permits exchanging samples without changing the beam shield or alternatively, exchanging beam shields without changing samples to allow introduction of new samples and replacement of worn beam shields.

In another embodiment of the invention, the beam shield may include multiple slits or diffractive elements, resulting in the creation of defined recesses in the sample at desired intervals. The beam shield may incorporate a louvered stack of multiple slats periodically spaced to enable material removal at defined intervals. If the louvered slats have an optimal angle and narrow enough periodicity, they may result in diffraction of the beam resulting in very thin samples which would be suitable for TEM (Transmission electron microscope) analysis.

The beam shield may be manufactured of any material having sufficient durability to withstand repeated exposure to the energy beam. In particular, the beam shield may be manufactured using a refractory or crystalline material having optimal optical and/or sputter-resistant properties. Alternatively, the beam shield may be prepared using a relatively inexpensive material that may not possess beam-resistant properties, thereby requiring the deposition of a refractory or crystalline coating onto the material. The coating may be applied by any conventional method, including evaporation, chemical vapor deposition, or powder coating followed by polishing using any of a variety of polishing techniques.

Figure 6:
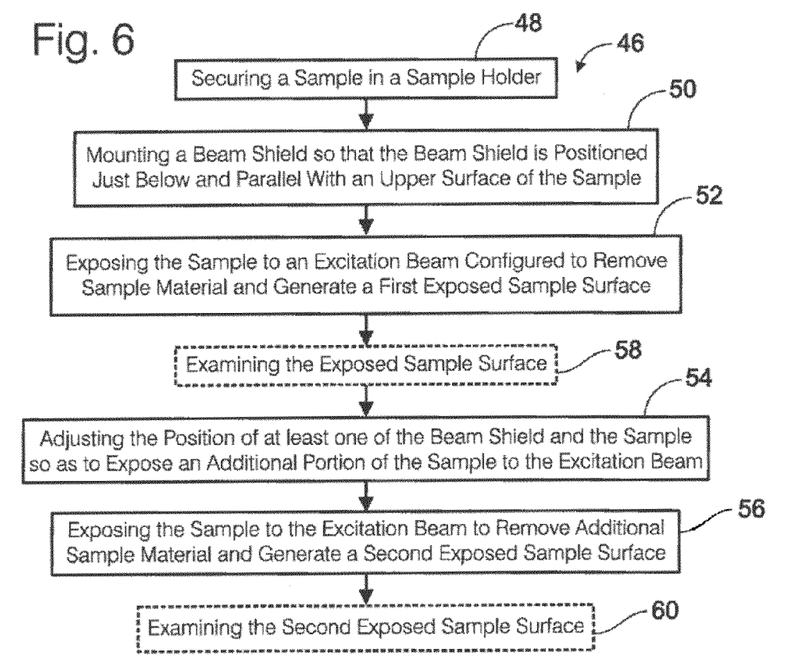
FIG. 6 is a flowchart illustrating a method of sample preparation according to an embodiment of the present invention.

The disclosed apparatus lends itself to a method of sample preparation, as represented in FIG. 6 by flowchart 46. The method includes securing a sample in a sample holder, at 48; mounting a beam shield so that the beam shield is positioned just below and parallel with an upper surface of the sample, at 50; exposing the sample to an excitation beam configured to remove sample material and generate a first exposed sample surface, at 52 additional portion of the sample to the excitation beam, at 54; and exposing the sample to the excitation beam to remove additional sample material and generate a second exposed sample surface, at 56. The method of flowchart 46 optionally includes examination of the sample surface. More specifically, upon generating the first exposed sample surface, the method optionally includes examining the exposed sample surface, at 58. Similarly, after generating the second exposed sample surface, the method optionally includes examining the second exposed sample surface, at 60.

As the sample may be incrementally exposed, revealing progressively deeper portions of the sample, the newly exposed sample surface may be examined after every exposure. In this way information about the overall structure of the sample can be obtained, leading to an understanding of the three-dimensional composition and morphology of the sample.

The system and method of the present invention may include one or more of the following exemplary embodiments:

A surface preparation system comprising a microscope sub stage, a beam shield, a beam shield holder and an excitation beam wherein the apparatus prepares substantially planar surfaces on solid samples.

A surface preparation system wherein the microscope sub-stage, sample holder, beam shield holder, and beam shield are mounted inside the vacuum chamber of the "host" analytical or other scientific instrument.

A surface preparation system wherein a real time viewing microscope (LM, SEM, FIB, or AFM) exists for monitoring the progress of the ongoing surface preparation.

A surface preparation system wherein the excitation beam is a produced by an excitation source (ion, electron, or laser) configured to produce an energy beam, transmit the beam through a vacuum interface, and focus the beam onto the beveled beam shield and exposed surface of the sample in either a pulsed or continuous mode.

A surface preparation system wherein the microscope sub-stage comprises a positive-positioned, self-aligning sample holder, a movable beam shield holder, and a beam shield; where at least one of the sample holder and the beam shield holder are configured to position a sample area of interest and top edge of the beam shield in the exact coincident point for processing and viewing.

A surface preparation system wherein the beam shield holder holds and clamps the beam shield in a position just below, and parallel with, the sample's top surface.

A surface preparation system wherein the beam shield holder can move the beam shield in the vertical direction with respect to the sample in increments of less than 1 μm per step.

A surface preparation system wherein the sample holder can move the sample in the vertical direction with respect to the beam shield in increments of less than 1 μm per step.

A surface preparation system wherein the beam shield holder is configured such that the beam shield can be easily changed in order to accommodate wear or to employ the use of alternate materials optimized for alternate excitation sources.

A surface preparation system wherein the beam shield is composed of a material that is processed to have a highly reflective beveled surface that is resistant to photon ablation and has a low coefficient of sputtering.

A surface preparation system wherein the beam shield can be unclamped from the sample, lowered a discrete vertical distance, then re-clamped to the sample in sequence to facilitate multiple milling cycles on sequentially lower regions of the sample.

A surface preparation system wherein the beam shield can also be a louvered shield or diffraction grating.

A surface preparation system wherein the beam shield can be moved laterally to expose un-processed surfaces that avoid the onset of deleterious artifacts resulting from over-etching of the beveled surface of the beam shield.

A method or preparing a sample coupon for microscopic cross section or planimetric analysis including steps to mount the sample in the sample holder, mount the beam shield in the beam shield holder, position the beam shield holder and/or sample holder such that the beam shield is just below the sample surface, bombard the sample and beam shield with a excitation beam for removing material, view or analyze the process results in real time, move the beam shield and/or sample holder to expose incrementally more of the sample, and repeat the process one or more times.

A method of sample preparation wherein a lateral beam strikes the beveled beam shield or diffractive element and exposed sample surface removing a thin layer of the sample surface approximately equivalent to the height of the gap between the sample and the upper edge of the beam shield.

A method of sample preparation wherein the beam shield is unclamped, the sample is raised incrementally, and the beam shield re-clamped against the sample to enable sequential processing steps.

A method of sample preparation that further includes imaging and/or analyzing the sample using detectors or a viewing microscope during or after processing and without removing the sample from the microscope vacuum chamber.

A method of sample preparation, wherein the viewing microscope is a SEM, FIB, LM or AFM and may incorporate multiple data acquisition detectors for chemical or morphometric analysis, including three dimensional reconstruction.

A method of sample preparation, wherein a thin bi-beveled beam shield or diffraction grating can be installed that allows parallel milling of two or more trenches in a sample to create thin lamella for light or transmission electron microscopy.

A method of sample preparation, wherein a louvered beam shield or diffraction grating can be installed in place of the beam shield for preparing alternating, sequential slices in a sample for light microscopy or electron microscopy.

This disclosure describes various sample preparation systems and methods for their use. However, many alternatives and modifications which may or may not be expressly mentioned are enabled, implied, and accordingly covered by the spirit of the disclosure. For example, although microscopy is mentioned repeatedly herein, it should be understood that a variety of analytical techniques may be facilitated by the present systems and methods.

The subject matter of the disclosure includes all novel and non-obvious combinations and subcombinations of the various elements, features, functions and/or properties disclosed herein. Similarly, where the disclosure recites "a" or "a first" element or the equivalent thereof, such disclosure should be understood to include incorporation of one or more such elements, neither requiring nor excluding two or more such elements. Novel and non-obvious combinations and subcombinations of features, functions, elements and/or properties may be claimed through presentation of claims in a related application.

What is claimed is:

1. A sample preparation system comprising:
a sample support, configured to secure a solid sample;
an excitation beam source that generates an excitation beam that includes an unfocused beam of ions, and that is configured to remove material from a surface of the solid sample;
a beam shield lens configured to deflect the excitation beam, wherein the beam shield lens generates an electromagnetic or electrostatic field to act as a linear lens for deflecting an ion beam and avoid sputtering of the beam shield lens; and
a beam shield holder configured to secure the beam shield lens so that an upper edge of the beam shield lens is positioned just below and parallel with the upper surface of the solid sample;
wherein the sample preparation system is mounted inside a scanning electron microscope.

2. The sample preparation system of claim 1, wherein the sample preparation system is mounted within a scanning electron microscope or charged particle beam instrument that incorporates an electron beam, wherein the electron beam is configured for imaging the solid sample.

3. The sample preparation system of claim 2, wherein the electron beam is configured for imaging the solid sample without a protective shutter.

4. The sample preparation system of claim 1, wherein the excitation beam source is configured to generate an energy beam that is either pulsed or continuous, focused or unfocused, and to transmit the energy of the excitation beam through a vacuum interface, and direct the energy beam onto an exposed surface of the sample.

5. The sample preparation system of claim 1, wherein the beam shield lens holder is configured to permit vertical adjustment of the beam shield lens in order to vary one or more of the position, strength, and horizontal linearity of an electromagnetic or electrostatic field used to deflect the excitation beam.

6. The sample preparation system of claim 5, wherein the beam shield holder is configured to permit vertical adjustment of the beam shield lens with respect to the solid sample in increments of less than about 1 μm.

7. The sample preparation system of claim 5, wherein the vertical position of the beam shield lens can be iteratively adjusted by unclamping the beam shield lens, moving the beam shield lens incrementally downward, and reclamping the beam shield lens, so that multiple surface processing cycles can be performed on sequentially lower regions of the sample.

8. The sample preparation system of claim 1, wherein the sample holder is vertically adjustable, and is configured to secure the sample so that an upper edge of the beam shield lens is positioned just below and parallel with the upper surface of the solid sample.

9. The sample preparation system of claim 1, wherein the position of the beam shield lens or the position of the sample is laterally adjustable, in order to expose an unprocessed surface of the sample or a surface of an additional sample held in a position adjacent to the sample.

10. The sample preparation system of claim 1, wherein the sample preparation system is mounted within a vacuum chamber of a scanning electron microscope or charged particle analytical tool having an electron beam, and the sample preparation system is configured to adjust the relative positions of the beam shield lens and the sample so that an upper edge of the beam shield lens can be positioned just below and parallel to an upper surface of the solid sample, and the relative positions of the beam shield lens and sample can subsequently be incrementally adjusted to permit the preparation of multiple prepared sample surfaces in sequentially lower regions of the sample.

11. A sample preparation system comprising:
a sample support, configured to secure a solid sample;
an excitation beam source that generates an excitation beam that includes an unfocused beam of ions, and that is configured to remove material from a surface of the solid sample;
a beam shield lens configured to protect the solid sample from the excitation beam, wherein the beam shield lens generates an electromagnetic or electrostatic field to act as a linear lens for deflecting an ion beam and avoid sputtering of the beam shield lens; and
a beam shield holder configured to secure the beam shield lens so that an upper edge of the beam shield lens is positioned lust below and parallel with the upper surface of the solid sample;
wherein a position of least one of the beam shield lens and the sample support is incrementally adjustable with respect to the other both horizontally and vertically; and
wherein the sample preparation system is mounted within a vacuum chamber of a scanning electron microscope or charged particle analytical instrument having an electron beam configured to monitor the solid sample.

12. A sample preparation system comprising:
a sample support, configured to secure a solid sample;

an excitation beam source that generates an unfocused ion beam configured to remove material from a surface of the solid sample;

a beam shield lens configured to deflect and shape the excitation beam, wherein the beam shield lens generates an electromagnetic or electrostatic field to act as a linear lens for deflecting an ion beam and avoid sputtering of the beam shield lens; and a beam shield holder configured to secure the beam shield lens so that an upper edge of the beam shield lens is positioned just below and parallel with the upper surface of the solid sample;

wherein a position of at least one of the beam shield and the sample support is incrementally adjustable with respect to the other both horizontally and vertically; and wherein the sample preparation system is mounted within a vacuum chamber of a scanning electron microscope or charged particle analytical instrument having an electron beam configured to monitor the solid sample.

13. A method of preparing an analytical sample, comprising:

securing a sample in a sample holder within a vacuum chamber of a scanning electron microscope, a focused ion beam microscope, or an X-Ray microscope;

mounting a beam shield lens so that an upper edge of the beam shield is positioned just below and parallel with an upper surface of the sample, wherein the beam shield lens generates an electromagnetic or electrostatic field to act as a linear lens for deflecting an ion beam and avoid sputtering of the beam shield lens;

exposing the sample to an excitation beam that includes an unfocused beam of ions, and that is configured to remove sample material and generate a first exposed sample surface;

adjusting the position of at least one of the beam shield lens and the sample so as to expose an additional portion of the sample to the excitation beam; and exposing the sample to the excitation beam to remove additional sample material and generate a second exposed sample surface.

14. The method of claim 13, wherein the exposed sample surfaces are examined in situ and without opening the vacuum chamber.

15. The method of claim 13, wherein the step of adjusting the position of at least one of the beam shield lens and the sample includes adjusting the vertical position of at least one of the beam shield lens and the sample; and the steps of adjusting the position of at least one of the beam shield lens and the sample and exposing an additional portion of the sample to the excitation beam are repeated sequentially multiple times, and the exposed portions of the sample are examined in situ and without opening the vacuum chamber.

16. The method of claim 13, wherein the step of adjusting the position of at least one of the beam shield lens and the sample includes adjusting the horizontal position of at least one of the beam shield lens and the sample; and the steps of adjusting the position of at least one of the beam shield lens and the sample and exposing an additional portion of the sample to the excitation beam are repeated sequentially multiple times, and the exposed portions of the sample are examined in situ and without opening the vacuum chamber.

17. The method of claim 13, further comprising alternating cycles of surface processing and examination of the exposed sample surface using a scanning electron microscope, a focused ion beam microscope, or an atomic force microscope in situ and without opening the vacuum chamber.

18. The method of claim 13, wherein examining the exposed sample surface includes the acquisition of at least one microscopic reference image directly following a surface processing cycle and before venting the vacuum chamber.

19. The method of claim 18, wherein the first and second exposed sample surfaces are examined without removing the sample from the sample holder or venting the vacuum chamber.

20. The method of claim 18, further comprising chemical or morphometric analysis of the exposed sample surfaces either during processing or immediately following processing and without venting the vacuum chamber.

21. The method of claim 17, further comprising generating a three-dimensional model of the sample, where the three-dimensional model is constructed from algorithmic assembly of data acquired at sequential sample surface layers.

22. A method of preparing an analytical sample, comprising:

securing a sample in a sample holder;

mounting a beam shield lens that includes a plurality of slits so that the beam shield is positioned adjacent to and parallel with an upper surface of the sample;

exposing the sample to an excitation beam that includes an unfocused beam of ions, the excitation beam being configured to remove sample material and thereby generating alternating and sequential slices in the sample;

wherein the beam shield lens generates an electromagnetic or electrostatic field to act as a linear lens for deflecting an ion beam and avoid sputtering of the beam shield lens; and wherein the beam shield holder is configured to secure the beam shield lens so that an upper edge of the beam shield lens is positioned lust below and parallel with the upper surface of the solid sample.

23. The method of claim 22, wherein the beam shield lens is a diffraction grating.

* * * * *